United States Patent [19]

Omata et al.

[11] Patent Number: 5,024,832
[45] Date of Patent: Jun. 18, 1991

[54] TERMITES TRAIL-FOLLOWING PHEROMONE AND A SAME COMPOSITION AND METHOD OF DETECTING CAPTURED TERMITES BY USING THIS COMPOSITION

[75] Inventors: Tetsuo Omata; Shuji Senda; Tamaki Tanaka; Eriko Kumagai; Chikara Kajimoto; Yutaka Nakazono, all of Osaka, Japan

[73] Assignee: Nitto Denko Co. Ltd., Osaka, Japan

[21] Appl. No.: 450,112

[22] Filed: Dec. 13, 1989

[30] Foreign Application Priority Data

Dec. 27, 1988 [JP] Japan .............................. 63-334090
Apr. 1, 1989 [JP] Japan .................................. 1-96998

[51] Int. Cl.⁵ ..................... A01N 25/00; A01N 25/08; A01N 31/00
[52] U.S. Cl. ..................................... 424/84; 424/410; 424/405; 424/DIG. 8; 424/DIG. 11; 514/724; 514/784
[58] Field of Search ........... 424/405, 407, 84, DIG. 8, 424/DIG. 11, DIG. 10, 410; 514/724, 784

[56] References Cited

U.S. PATENT DOCUMENTS 3,888,982 6/1975 Kenaga .............................. 514/188

FOREIGN PATENT DOCUMENTS 044138 4/1981 Japan .

OTHER PUBLICATIONS

Selective Proton Transfer of Unsaturated Esters, Ikeda et al., Tetrahedron 43, 743 (1987).
Chemical Identification of the Trail Following Pheromone, Tai. et al., J. Org. Chemistry 34, 2180, 1969.
Tetrahedron, vol. 43, No. 4, pp. 743-753, 1987.
The Journal of Organic Chemistry, vol. 34, No. 7, pp. 2180-2182.

Primary Examiner—Thurman Page
Assistant Examiner—G. S. Kishore
Attorney, Agent, or Firm—Armstrong, Nikaido, Marmelstein, Kubovcik & Murray

[57] ABSTRACT

A termites trail-marking pheromone which is (3Z,6Z,8E)-dodecatrienol, and a composition which comprises (3Z,6Z,8E)-dodecatrienol as an essential component and another component which is a trail-marking pheromone-like substance, and a method of detecting termites by using this composition or (3Z,6Z,8E)-dodecatrienol.
The trail-marking pheromone and composition are highly safe in that they have no residual toxicity, and they have a stable, long-term trail-marking effect for termites. This invention provides a simple and rapid method of detecting termites, and a simple and effective method of capturing termites.

2 Claims, 2 Drawing Sheets

TERMITES TRAIL-FOLLOWING PHEROMONE AND A SAME COMPOSITION AND METHOD OF DETECTING CAPTURED TERMITES BY USING THIS COMPOSITION

FIELD OF THE INVENTION

This invention relates to a termite trail pheromone, a composition, and method of detecting termites by using this composition. The object of this invention is to provide a termite trail pheromone and a composition which are highly safe, having no residual toxicity, and have a stable, long-term trail-marking effect on termites.

Another object is to provide a simple and rapid method of detecting termites by using a termite trail pheromone and composition.

Yet another object is to provide a simple and effective method of exterminating termites by using a termite trail-marking pheromone and composition.

BACKGROUND OF THE INVENTION

In Japan, there are a number of termite species such as House termite (*Coptotermes formosanus* Shiraki), Japanese subterranean termite (*Reticulitermes speratus* (Kolbe)), Satsuma termite (*Glyptotermes satsumensis* Matsumura), Katan termite (*Glyptotermes fuscus* Oshima), Large termite (*Hodotermopsis japonica* Halmgreu) et al.

Especially, the House termite (*Coptotermes formosanus* Shiraki) and Japanese subterranean termite (*Reticulitermes speratus* (Kolbe)), which are classified as Pterygota Neoptera Isoptera, are widespread in Japan.

It has become an issue that serious damages are caused by House termites living in the west of Japan in the kanto districts, which feed on houses, timbers, and sometimes important cultural assets.

Additionally, Japanese subterranean termites living all over Japan except the Hokkaido districts feed on wood beams, wood bases of houses, and cross-tie timber.

It is said that the total amount of the damages caused by House termites and Japanese subterranean termites in Japan is 200,000,000,000 ¥/year, so that termites need to be captured or exterminated.

BRIEF DESCRIPTION OF THE PRIOR ART

Considering the above situation, mothproofing is usually applied to timber, and further Aldrin, chlordane, dieldrin and like organic chlorine-type insecticides have been conventionally used to exterminate the termites.

However, all of the aforesaid termite exterminating methods have defects.

In the case of termites nesting in timber, like the Japanese subterranean termite, the method of using chlorine-type insecticides is not effective enough.

But in the case of termites making a colony in the earth far from feeding timber, like house termites, it is very difficult to locate the colony by home working, so that this type of termites is hardly exterminated because the termites colony must be located, dug out, and sprinkled with insecticides.

Further, said organic-chlorine type insecticides pose problems with respect to retention, toxicity and environmental pollution, and consequently the use of chlordane which is the major ingredient of miticides was completely banned on and after April, 1987.

Alternatively, chlorpyrifos and like organic phosphorus-type miticides have been used lately. These miticides, however, have problems in terms of acute toxicity, poor shelf like, etc.

Up to date, it is said that the most effective method of detecting termites is to unearth timber near the outside corridor of a house for about one month, but this method takes long and is not an exact detection method.

Therefore, there is a need for a trail-marking substance or composition which is highly safe, has no residual toxicity, and has a stable, long-term trail-marking effect for termites, and for a simple and rapid method of detecting termites to prevent damages, as well as a simple and effective method of capturing termites by using a termite trail-marking substance and composition.

Tetrahedron, Vol. 43, No. 4, Pages 743 to 753, published in 1987, discloses that a trail-marking pheromone for the Japanese subterranean termite can be stereoselectively synthesized by a method of deconjugative protonation of trienolates.

Journal of Organic Chemistry, Vol. 34, No. 7, Pages 2,180 to 2,182, discloses synthetic procedures for three isomers of a trail-marking pheromone for a southern subterranean termite.

SUMMARY OF THE INVENTION

The present invention relates to a termite trail-marking pheromone which is (3Z,6Z,8E)-dodecatrienol (of formula (1)), a composition which comprises (3Z,6Z,8E)-dodecatrienol (of formula (1)) as an essential component, and another component which is at least one selected from the group consisting of n-hexanoic acid, ethylene glycol monomethyl ether, diethylene glycol monoethyl ether, diethylene glycol monobutyl ether, p-hydroxysilicic acid, vanillic acid, protocatequinic acid, p-hydroxybenzoic acid, β-carotene and 3-hexen-1-ol, and a method of detecting termites by using this composition or (3Z,6Z,8E)-dodecatrienol (of formula (1)).

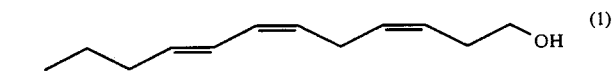

(1)

DETAILED DESCRIPTION OF THE INVENTION

Figure 1:
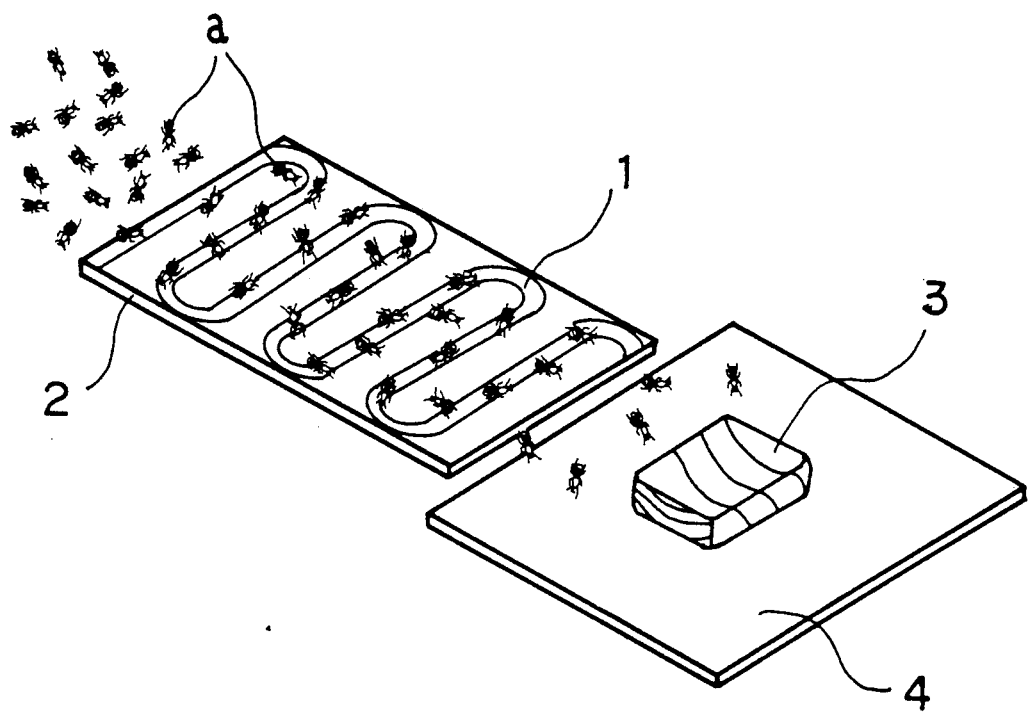
FIG. 1 is an illustrative view of an embodiment of the method of this invention for detecting termites.

In view of the aforementioned problems, the present inventors have conducted extensive research, and found that (3Z,6Z,8E)-dodecatrienol of the formula (1) acts as a trail-marking pheromone for not only widespread household noxious insects such as the Japanese subterranean termite, but also for the House termite which causes serious damages.

The trail-marking pheromone used herein is a chemical secretion by termites which provides marks or traces to lead termites back to a colony from which they had come, and to lead another of the same species to a bait found by the termites in their search.

It is known that social insects secrete this pheromone.

The present invention has been accomplished based on this finding.

From hereon in the description of this invention, the word "termites" includes both Japanese subterranean termites and House termites, except where otherwise indicated.

The present invention relates to a termites trail-marking pheromone which is (3Z,6Z,8E)-dodecatrienol (of formula (1)), and a composition which comprises (3Z,6Z,8E) dodecatrienol (of formula (1)) as an essential component, and another component which is at least one selected from the group consisting of n-hexanoic acid, ethylene glycol monomethyl ether, diethylene glycol monoethyl ether, diethylene glycol monobutyl ether, p-hydroxysilicic acid, vanillic acid, protocatequinic acid, p-hydroxybenzoic acid, β-carotene and 3-hexen-1-ol, and a method of detecting termites by using this composition or (3Z,6Z,8E)-dodecatrienol (of formula (1)).

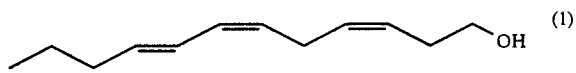

(1)

The present inventors have conducted extensive research and found that (3Z,6Z,8E)-dodecatrienol (of formula (1)) acts as a trail-marking pheromone for not only Japanese subterranean termites, but also House termites.

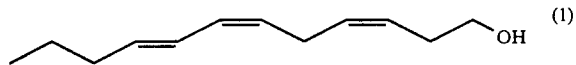

(1)

The (3Z,6Z,8E)-dodecatrienol (of formula (1)) is produced by a well-known synthetic process, such as (a) the process using a 3,4-epoxybutanol as a starting material and (b) the process using a butanal as a starting material.

The process (a) was described in J. Insec. Physiol., Vol 17, Pages 181 to 188, 1971, and the process (b) was described in J. Org. Chem., Vol. 34 (7), Pages 2,180 to 2,182.

(3Z,6Z,8E)-dodecatrienol (of formula (1)) may be used singly or in combination with the conventional attractants such as extracted materials from the rot of Serpula lacrymano, Lenzites trabea or rotten wood chips.

Further, (3Z,6Z,8E)-dodecatrienol may be used, to enhance the effect of the trail-marking pheromone, in combination with n-hexanoic acid, ethylene glycol monomethyl ether, diethylene glycol monoethyl ether, diethylene glycol monobutyl ether, p-hydroxysilicic acid, vanillic acid, protocatequinic acid, p-hydroxybenzoic acid, β-carotene, 3-hexene-1-ol, etc , which were found by the present inventors to enhance the activity of the trail-marking pheromone for Japanese subterranean termites and House termites.

To add the above said pheromone-like substances to (3Z, 6Z,8E)-dodecatrienol has the effect of reinforcing the inducing effect on the termites, in comparison with the use of the pheromone only.

In this invention, it is possible to detect or capture the termites with an adhesive after inducement using the above termites trail-marking composition, and a method to eradicate the whole colony of termites by taking advantage of their ecological behavior of taking and bringing bait impregnated with miticide back to a colony.

The method of detecting termites of this invention comprises the following steps;

(1) preparing the detecting material which is a combination of adhesive and (3Z,6Z,8E)- dodecatrienol or the aforesaid trail-marking composition, (2) setting this detecting material on or in the earth inside or near the house under conditions of high humidity, poor light and poor ventilation, (3) leaving this detecting material for certain term, (4) confirming the presence or absence of the termites by the presence or absence of captured termites on this detecting material.

The reason for setting the material on or in the earth inside or near the house under conditions of high humidity, poor light and poor ventilation stems from the ecological behavior of the termites.

The termites are attracted to construction timber which is connected to their colony by a termite tunnel in the earth or timber, and their colony is characterized by conditions of high humidity, poor light and poor ventilation.

Especially the termites dislike direct sunlight.

Further, the termites are attracted to construction timber near their colony which they have built in the same timber.

Therefore, setting the detecting material near their colony is very desirable.

The (3Z,6Z,8E)-dodecatrienol or trail-marking composition may be applied in any pattern, such as in a continuous or discontinuous line or circuitous line in a solid state. Another method is to apply them in the form of a laminate of their solid state and a base material. Yet another method is to apply them as a layer of a solution in an organic solvent like acetone spread on the base material.

(3Z,6Z,8E)-dodecatrienol is preferably used in an amount of $10^{-2}$ to $10^{-20}$ g/cm, more preferably in an amount of $10^{-7}$ to $10^{-17}$ g/cm at the spreading width mentioned hereafter.

The attractants or compounds active as a trail-marking pheromone or their mixture may be applied continuously or in a dotted line in a width of 10 μm to 5 mm, more preferably 50 μm to 1 mm.

When the mixture is applied in a dotted line, the intervals between dots must be shorter than the body length of the termites.

The adhesives to be used to entrap or detect termites with the use of the pheromone (3Z,6Z,8E)-dodecatrienol or the composition of the same are preferably set near the adhesive trap.

Further, in setting the adhesives to entrap or detect termites with the pheromone or the composition in or near the house, it is especially desirable to place them on the ground or the floor.

The base material to be applied with the pheromone or composition is not specifically limited, and examples thereof are: wax paper, cardboard, ground glass, plastic plate, stones, sand, concrete board, timbers, wood chips, yarn, cotton, cloth, synthetic paper, metal chips, metal plate or the like.

The adhesives to be used to entrap or detect termites with the use of the pheromone are not specifically limited as long as the adhesive captures termites attracted by the pheromone.

Such adhesives are butadiene-type and acrylic acid-type adhesives.

These adhesives may be painted directly on the base material or bait for termites such as wood.

The method of this invention for exterminating termites comprises the following steps:

(1) preparing the exterminating material which combines an adhesive and (3Z,6Z,8E)-dodecatrienol or the aforesaid trail-marking composition and termites miticides, (2) setting this exterminating material on or in the earth inside or near the house under conditions of high humidity, poor light and poor ventilation, (3) leaving this exterminating material for a certain term, whereby the termites are exterminated by this exterminating material.

Useful examples of miticides are chlorpyrifos, phomix, phridaphenthion, fluvalinate, fenpropathrin, permethrin isocyanurate and like organic phosphorus; pyresroid, carbamate, and fluorine derivatives such as molybdic acid, tungsten acid, alkaline metal salt, ω-fluroacetate derivative, long chain carboxylic acid, long chain unsaturated alcohol, etc.

The miticide to be used may be in a concentration of 0.1% to 40%, and may be used in the form of an aqueous solution, emulsion or even a stock solution.

Useful examples of stabilizers to make (3Z,6Z,8E)-dodecatrienol suitable for outdoor use for an extended period of time are BHT, hydroquinone catechol and the like.

The present invention will be described in more detail with reference to the following examples and comparisons.

EXAMPLE 1

A solution of (3Z,6Z,8E )-dodecatrienol in acetone (0.01 ppm) was meanderingly applied on ground glass (0.5 mm in width, 0.00001 g/cm in amount, 50 cm in length).

An adhesive trap having chips of a pine tree therein was placed at one end of the applied solution.

Sixty worker Japanese subterranean termites are released around the other end of the solution and allowed to stand for about 2 hours.

The number of the termites captured on the adhesive trap was found to be 41.

FIG. 1 illustrates this example, wherein numeral (1) indicates an acetone solution of (3Z,6Z,8E )-dodecatrienol, (2) is the ground glass, (3) is a chip of pine tree, (4) is an adhesive trap and (a) is a Japanese subterranean termite.

EXAMPLE 2

A similar test was conducted in the same manner as in Example 1 with the exception of using House termites in place of Japanese subterranean termites.

The number of the House termites captured on the adhesive trap was found to be 35.

EXAMPLES 3 TO 12 AND COMPARISON 1

Similar tests were conducted in the same manner as in Example 1 and 2 with the exception of using the substance described in the following Table 1, admixed with an acetone solution of (3Z,6Z,8E )dodecatrienol at the same concentration (that is 0.01 ppm).

Results of these tests are also described in Table 1.

Further, a similar test as Comparison 1 was conducted in the same manner as in Example 1 with the exception of the glass being applied with nothing.

The result for Comparison 1 is also described in Table 1.

TABLE 1

|  | substance | Japanese subterranean termites | House termites |
|---|---|---|---|
| Example 3 | n-hexanoic acid | 51 | 43 |
| Example 4 | ethylene glycol monomethyl ether | 52 | 50 |
| Example 5 | diethylene glycol monoethyl ether | 47 | 38 |
| Example 6 | diethylene glycol monobutyl ether | 49 | 44 |
| Example 7 | p-hydroxysilicic acid | 48 | 39 |
| Example 8 | vanillic acid | 51 | 26 |
| Example 9 | protocatequinic acid | 55 | 31 |
| Example 10 | p-hydroxybenzoic acid | 43 | 31 |
| Example 11 | β-carotene | 44 | 32 |
| Example 12 | 3-hexene-1-ol | 46 | 34 |
| Comparison 1 | nothing | 12 | 7 |

EXAMPLE 13

In a solution of 16-fluoro-9-(E)-hexadecen-1-ol, which is a termites miticide, in 0.1% acetone (10 ml) were immersed dried chips of a pine tree and the chips were dried in the atmosphere for one day.

The dried chips were thereafter placed on one end of a piece of ground glass which (3Z,6Z,8E )-dodecatrienol was applied (0.5 mm in width, 50 cm in full length, 0.00001 g/cm in amount).

A part of a wooden colony containing 120 Japanese subterranean termites was set at the other end of the piece of glass.

Wood chips free of miticide were placed around the wooden colony at the opposite side of the glass.

Figure 2:
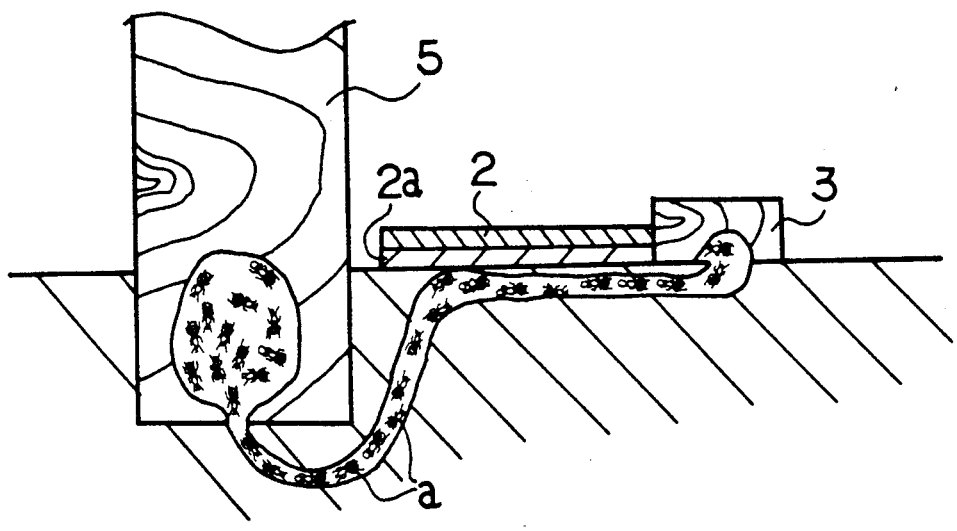
FIG. 2 is an illustrative view of an embodiment of the method of this invention for exterminating Japanese subterranean termites.

FIG. 2 illustrates this example, wherein numeral (2) is the ground glass, (2a) is the application face, (3) is a chip of pine tree, (5) is a timber tip in the termites colony, (a) is a Japanese subterranean termite.

The death ratio of termites in the wooden colony was checked with the passage of time every 5 days.

The result of this Example is described in Table 2.

Comparison 2 is a control blank wherein no pheromone inducement was effected between the wooden colony and the wood chips impregnated with miticide.

The result of this Comparison 2 is also described in Table 2.

TABLE 2

|  | after 5 days | after 10 days | after 20 days | after 30 days |
|---|---|---|---|---|
| Example 13 | 5% | 30% | 70% | 95% |
| Comparison 2 | 2% | 4% | 10% | 15% |

EXAMPLE 14

120 House termites were buried in earth at a depth of about 20 cm to make colony.

The dried chips were thereafter placed on one end of a piece of ground glass to which (3Z.6Z.8E)-dodecatrienol was applied as in Example 13.

Wood chips free of miticide were placed on the earth colony at the opposite side of the glass.

Figure 3:
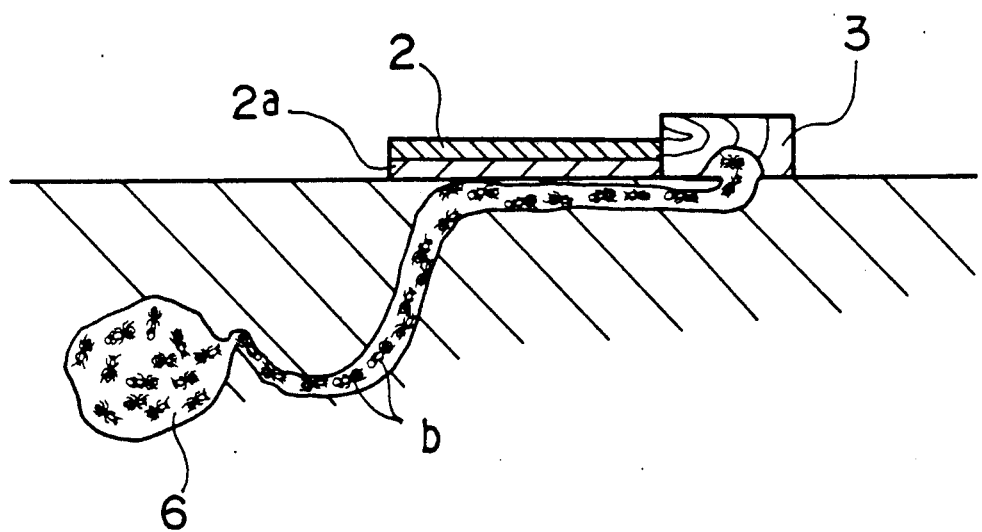
FIG. 3 is an illustrative view of an embodiment of the method of this invention for exterminating House termites.

FIG. 3 illustrates this example, wherein numeral (2) is a piece of ground glass, (2a) is the application face, (3)

is a chip of pine tree, (6) is a termites colony, (b) is a House termite.

The death ratio of termites in the colony was checked every 5 days.

The result of this Example is described in Table 3.

Comparison 3 is a control blank wherein no pheromone inducement was effected between the colony and the wood chips impregnated with miticide.

The result of this Comparison 3 is also described in Table 3.

TABLE 3

|  | after 5 days | after 10 days | after 20 days | after 30 days |
|---|---|---|---|---|
| Example 14 | 4% | 25% | 67% | 90% |
| Comparison 3 | 1% | 3% | 7% | 11% |

We claim:
1. A termite trail-marking composition, comprising:
(a) (3Z,6Z,8E)-dodecatrienol of formula (1)

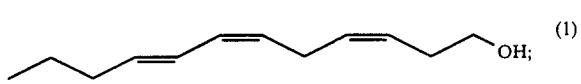

and (b) at least one member selected from the group consisting of n-hexanoic acid, p-hydroxysilicic acid, vanillic acid, protocatequinic acid, p-hydroxybenzoic acid, β-carotene and 3-hexen-1-ol.

2. A termite trail-marking composition as in claim 1, wherein component (a) and component (b) are dissolved in an organic solvent.

* * * * *

UNITED STATES PATENT AND TRADEMARK OFFICE
CERTIFICATE OF CORRECTION

PATENT NO. : 5,024,832

DATED : June 18, 1991

INVENTOR(S) : OMATA et al

It is certified that error appears in the above-identified patent and that said Letters Patent is hereby corrected as shown below:

On the title page, Item [30], "April 1", should read -- April 17--.

Signed and Sealed this

Third Day of November, 1992

Attest:

DOUGLAS B. COMER

*Attesting Officer*     Acting Commissioner of Patents and Trademarks